US005248770A

United States Patent [19]
Jacobson et al.

[11] Patent Number: 5,248,770
[45] Date of Patent: Sep. 28, 1993

[54] MOLECULAR PROBES FOR ADENOSINE RECEPTORS

[75] Inventors: Kenneth A. Jacobson, Silver Spring, Md.; John W. Daly, Washington, D.C.; Kenneth L. Kirk, Bethesda, Md.

[73] Assignee: The United States of America, as represented by the Department of Health and Human Services, Washington, D.C.

[21] Appl. No.: 287,539

[22] Filed: Dec. 19, 1988

Related U.S. Application Data

[63] Continuation of Ser. No. 874,143, Jun. 13, 1986, abandoned, which is a continuation-in-part of Ser. No. 717,616, Mar. 29, 1985, Pat. No. 4,696,932, which is a continuation-in-part of Ser. No. 664,953, Oct. 26, 1984, Pat. No. 4,612,315, said Ser. No. 874,143, continuation-in-part of Ser. No. 833,035, is a continuation-in-part of Ser. No. 717,624, Mar. 29, 1985, abandoned.

[51] Int. Cl.$^5$ .................... A61K 31/52; C07D 473/06
[52] U.S. Cl. .................... 536/26.1; 536/22.1; 536/26.12; 536/26.13; 530/330; 530/331; 530/332; 260/998.2
[58] Field of Search .................... 536/24, 26; 514/46, 514/7; 530/324, 325, 326, 327

[56] References Cited

U.S. PATENT DOCUMENTS 4,612,315  10/1984  Jacobson ............................. 514/263
4,696,932   3/1985  Jacobson ............................. 514/263

Primary Examiner—Johnnie R. Brown
Assistant Examiner—James O. Wilson
Attorney, Agent, or Firm—Susan S. Rucker; Gerald M. Murphy, Jr.

[57] ABSTRACT

This application discloses probes for adenosine receptors which are functionalized congeners of the following compound:

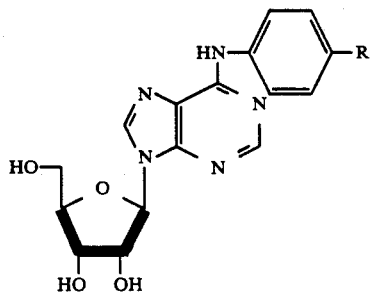

wherein R is —CH$_2$—C(O)—R' or

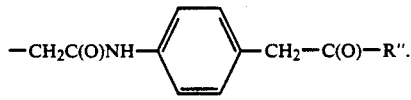

These probes bind to A$_2$ and A$_3$ adenosine receptors and aid in quantifying and characterizing the receptors. The compounds may be labeled, for example with fluorescent compounds or radioactive compounds, or unlabeled.

14 Claims, 9 Drawing Sheets

XAC = $-H_2N(CH_2)_2NH-COCH_2-O-\phenyl-$8-(1,3-dipropylxanthine) ⟩ 2

ADAC = ⟩ 1

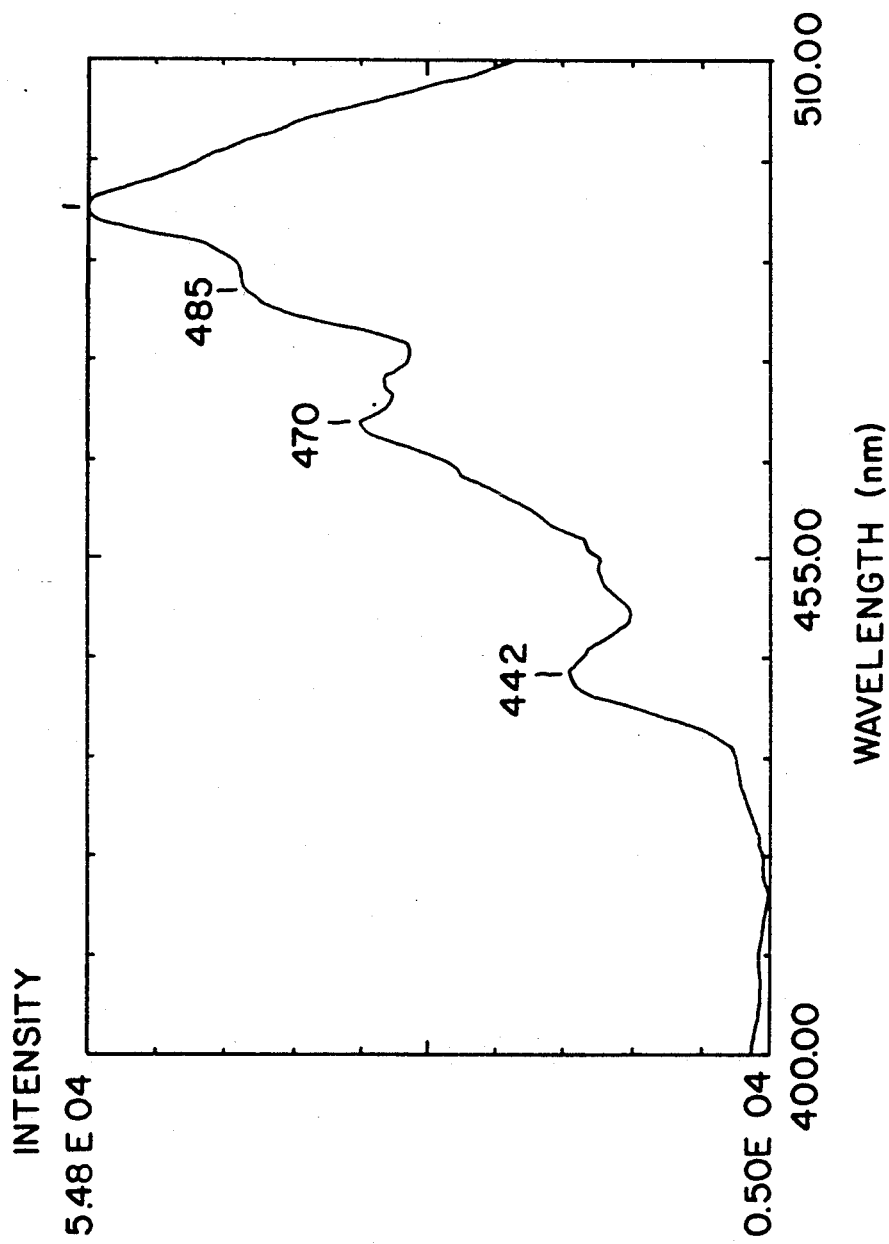

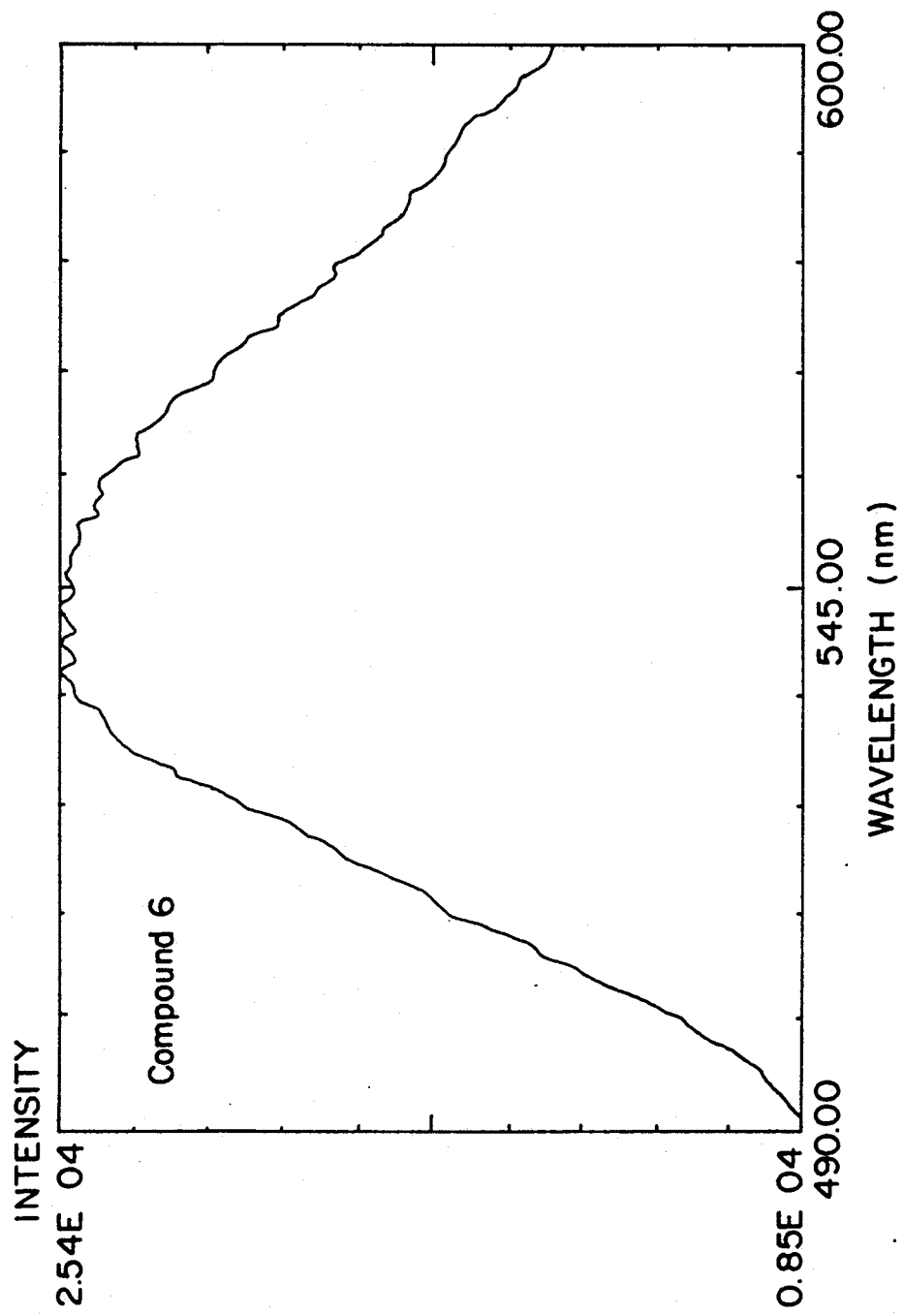

RADIOIODINATION OF AN AMINO ACID CONJUGATE USING A PROSTHETIC GROUP

MOLECULAR PROBES FOR ADENOSINE RECEPTORS

CROSS REFERENCE TO RELATED APPLICATIONS

This application is a continuation of Ser. No. 06/874,143 filed Jun. 13, 1986 now abandoned, which is a CIP of Ser. No. 06/717,616 filed Mar. 29, 1985 now U.S. Pat. No. 4,696,932, which is a Continuation In Part of Ser. No. 06/664,953 filed Oct. 26, 1984 now U.S. Pat. No. 4,612,315; and Ser. No. 06/874,143 is a Continuation In Part of Ser. No. 06/833,035 filed Feb. 26, 1986 now abandoned, which is a Continuation In Part of Ser. No. 06/717,624 filed Mar. 29, 1985 now abandoned.

BACKGROUND

In the four copending applications above there are disclosed functionalized congeners of $N^6$-phenyladenosine and 1,3-dialkyl-8-phenyl xanthine and in which a spacer chain terminating in a chemical functional group is inserted at the para position of the phenyl for the purpose of enhancing the binding properties of the functionalized congener to the A-1 adenosine receptor site or the A-2 adenosine receptor, depending upon the drug properties of the drug portion or primary pharmacophore of the molecule. In the case of adenosine the pharmacophore is an agonist. In the case of xanthine the pharmacophore is an antagonist. Both adenosine and xanthine derivatives bind competitively to A-1 and A-2 adenosine receptors.

UTILITY STATEMENT

The present application prepares and describes probes radioactive and non-radioactive for more sensitive assay-type quantitative binding measurements of A-1 and A-2 receptors using the functionalized congeners described and claimed in the four above-named copending applications.

MATERIAL INFORMATION DISCLOSURE

The art below, taken individually or collectively, does not show the specific congener compounds or effects of the present invention.

Daly, "Adenosine Receptors: Targets for Future Drugs," *Journal of Medicinal Chemistry*, 25(3):197–207, March 1982.

Kikugawa, et al, "Platelet Aggregation Inhibitors. $N^6$-Substituted Adenosines," *Journal of Medicinal Chemistry*, 16(4):358–364, 1973.

Bruns, et al, "Adenosine Receptor Interactions and Anxiolytics," *Neuropharmacology*, 22(12B):1523–1529, 1983.

Bruns, et al, "Adenosine Receptors in Brain Membranes: Binding of $N^6$-cyclohexyl[$^3$H]adenosine and 1,3-diethyl-8-[$^3$H]phenylxanthine," *Proc. Natl. Acad. Sci. USA*, 77(9):5547–5551, September 1980.

The cited reference discuss adenosine receptors in isolated preparations for research purposes.

BRIEF DESCRIPTION OF THE DRAWINGS

FIG. 2 (b) shows saturation of [$^3$H]ADCA binding to cerebral cortex from a calf. Specific and non-specific binding was determined for 120 min. at 37° C. Values are means of a typical experiment done in triplicate. Right panels: Scatchards plots of the same data. $K_D$ (nM) and $B_{max}$ (pmol/mg protein) were 1.4 and 0.57, respectively, for rat and 0.34 and 0.64, respectively, for calf cerebral cortex membranes.

FIG. 4 (b) shows the effect of adenosine analogs on adenylate cyclase activity of human platelet membranes. Adenylate cyclase was measured for 10 min. at 37° C. Values are means of a typical experiment done in triplicate. The $EC_{50}$-values were 100 nM and 240 nM for NECA and 800 nM and 980 nM for ADAC in PC12 and platelet membranes, respectively.

FIG. 5 (a) shows the fluorescene emission curve for compounds 3 and 6 (SPEX, spectrophotometer, pH7 aqueous buffer).

FIG. 5 (b) shows the intensity of fluorescence emission of compound 3 at various concentrations.

FIG. 7 (b) shows the spectra of compound 11, (CD$_3$)$_2$SO Varian.

SUMMARY OF THE INVENTION

Figure 1:
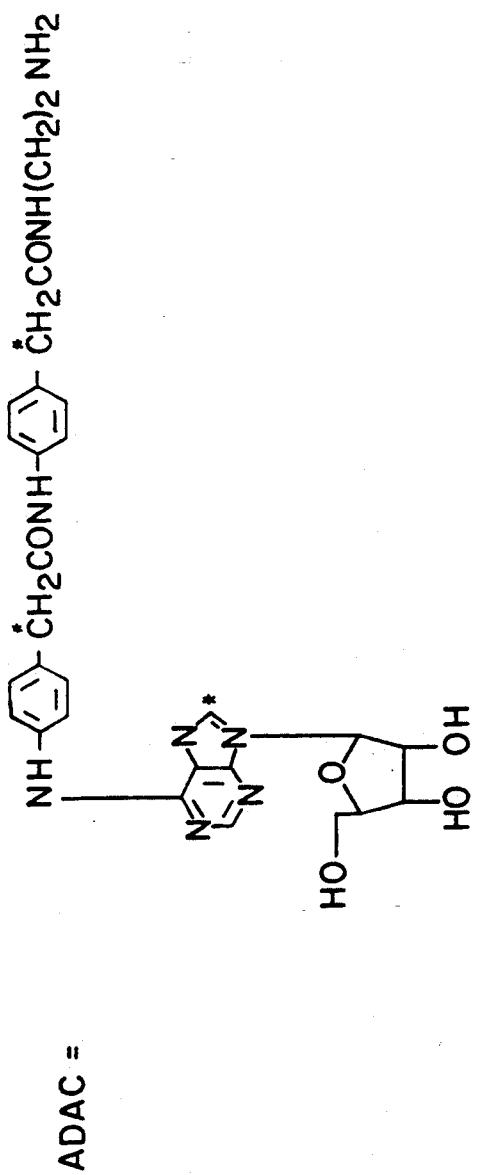
FIG. 1 shows structures and sites of tritiation of the functionalized congeners which are potent adenosine receptor agonist (1, ADAC) and antagonist (2, XAC) analogs.
Figure 2A:
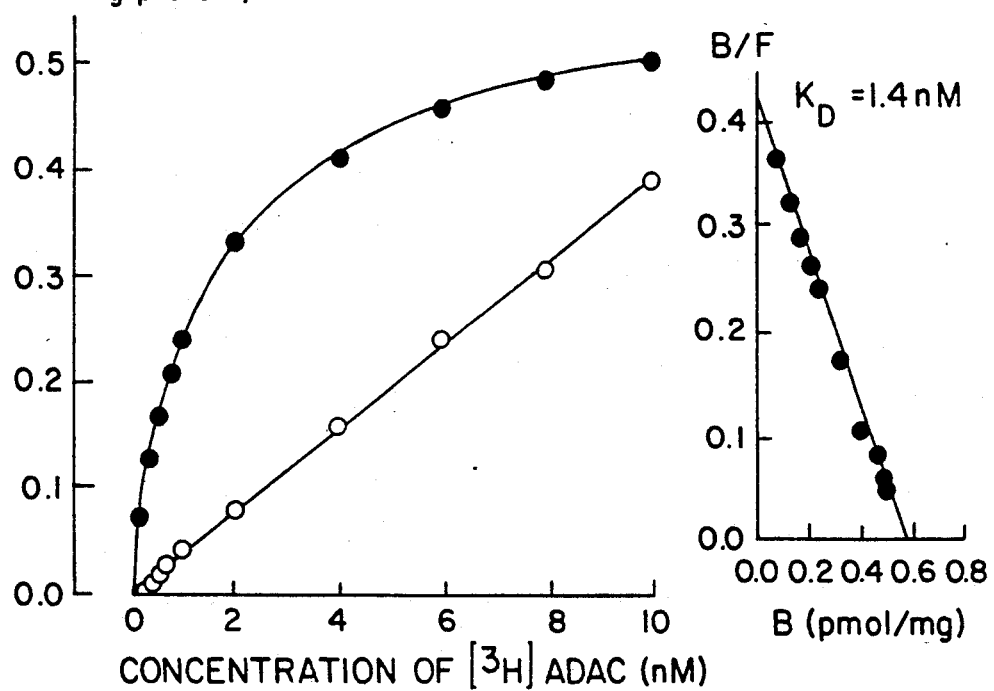
FIG. 2 (a) shows saturation of [$^3$H]ADAC binding to cerebral cortex membranes from a rat.
Figure 2B:
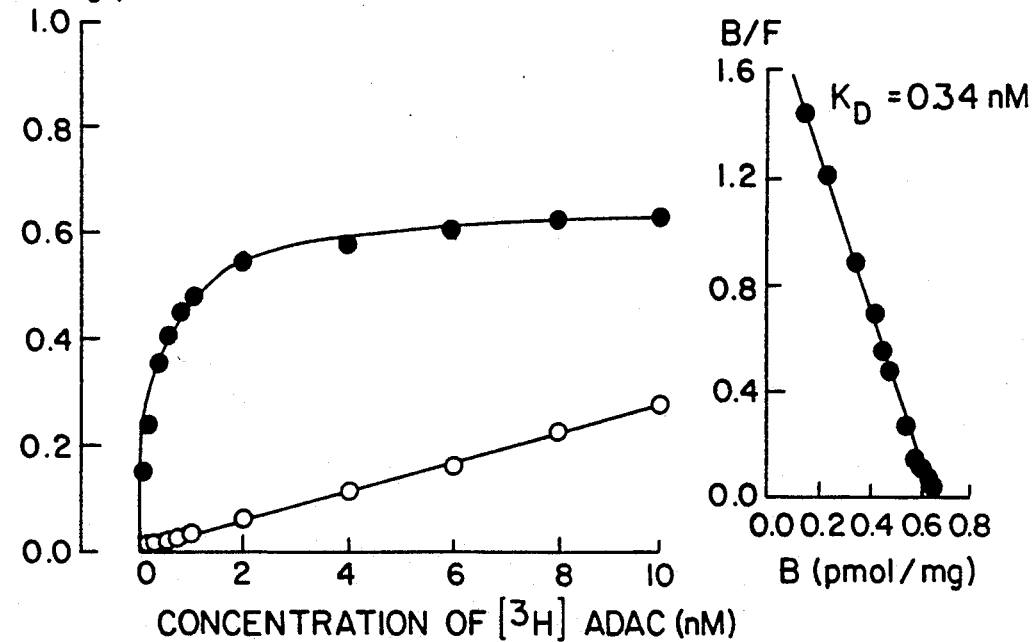
Figure 3:
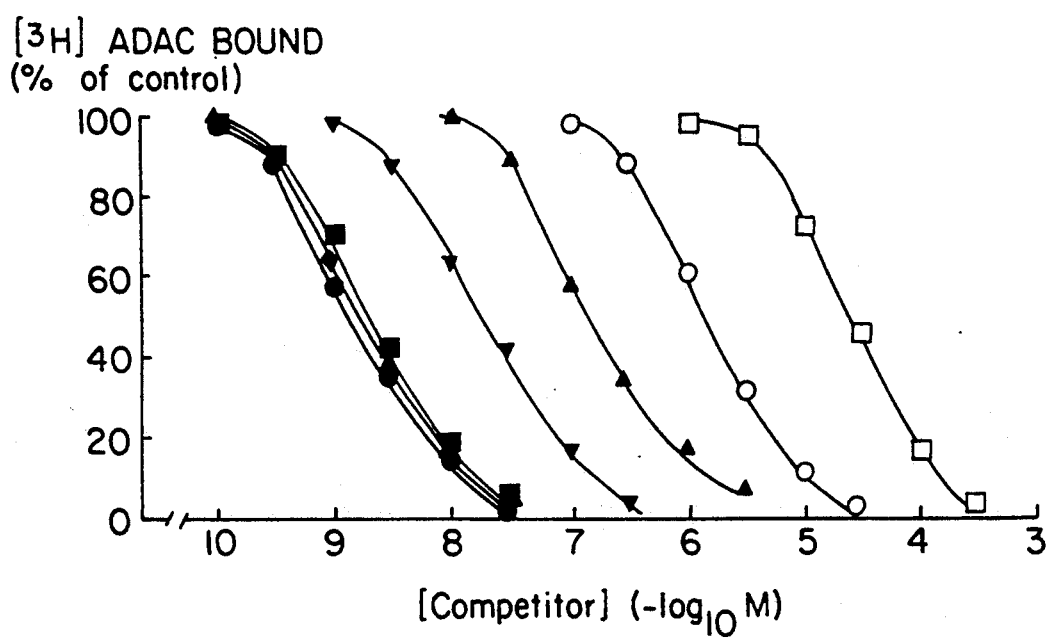
FIG. 3 shows the inhibition of [$^3$H]ADAC binding to rat cerebral cortex membranes by adenosine agonists and antagonists. Binding of 1 nM [$^3$H]ADAC was measured for 120 min. at 37° C. Values are from a typical experiment done in triplicate. Curves are shown for ADAC ●; for R-PIA ◆; for XAC ■; for NECA ▼; for 1,3-dipropyl-8-(p-sulfophenyl)xanthine ▲; for 8-(p-sulfo-phenyl)theophylline ○; for theophylline □.
Figure 4A:
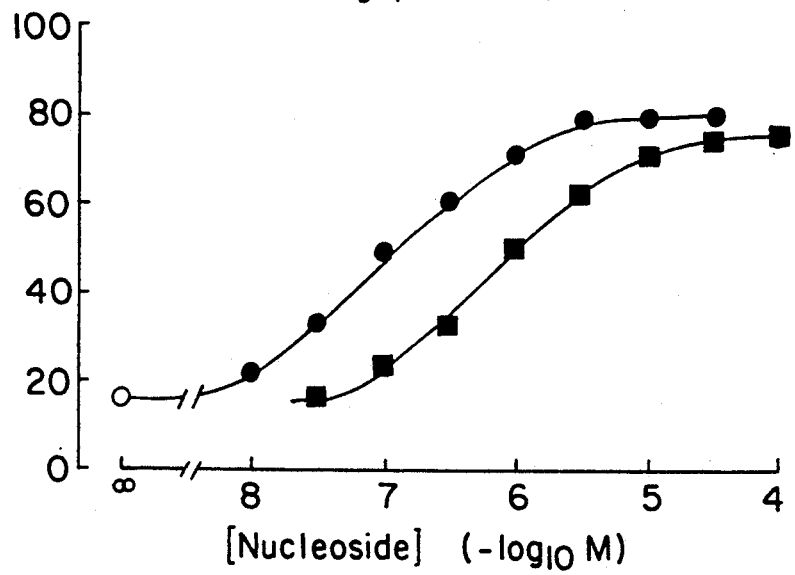
FIG. 4 (a) shows the effect of adenosine analogs on adenylate cyclase activity of rat pheochromocytoma (PC12) cells.
Figure 4B:
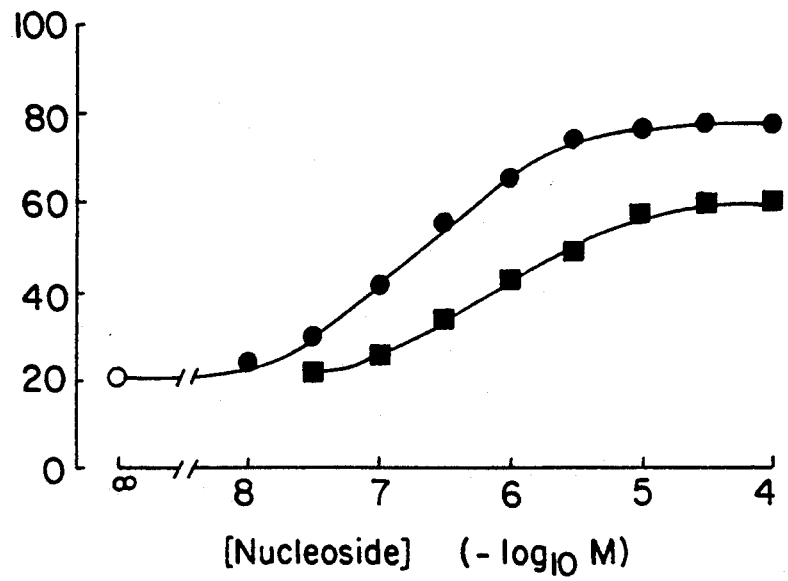
Figure 6:
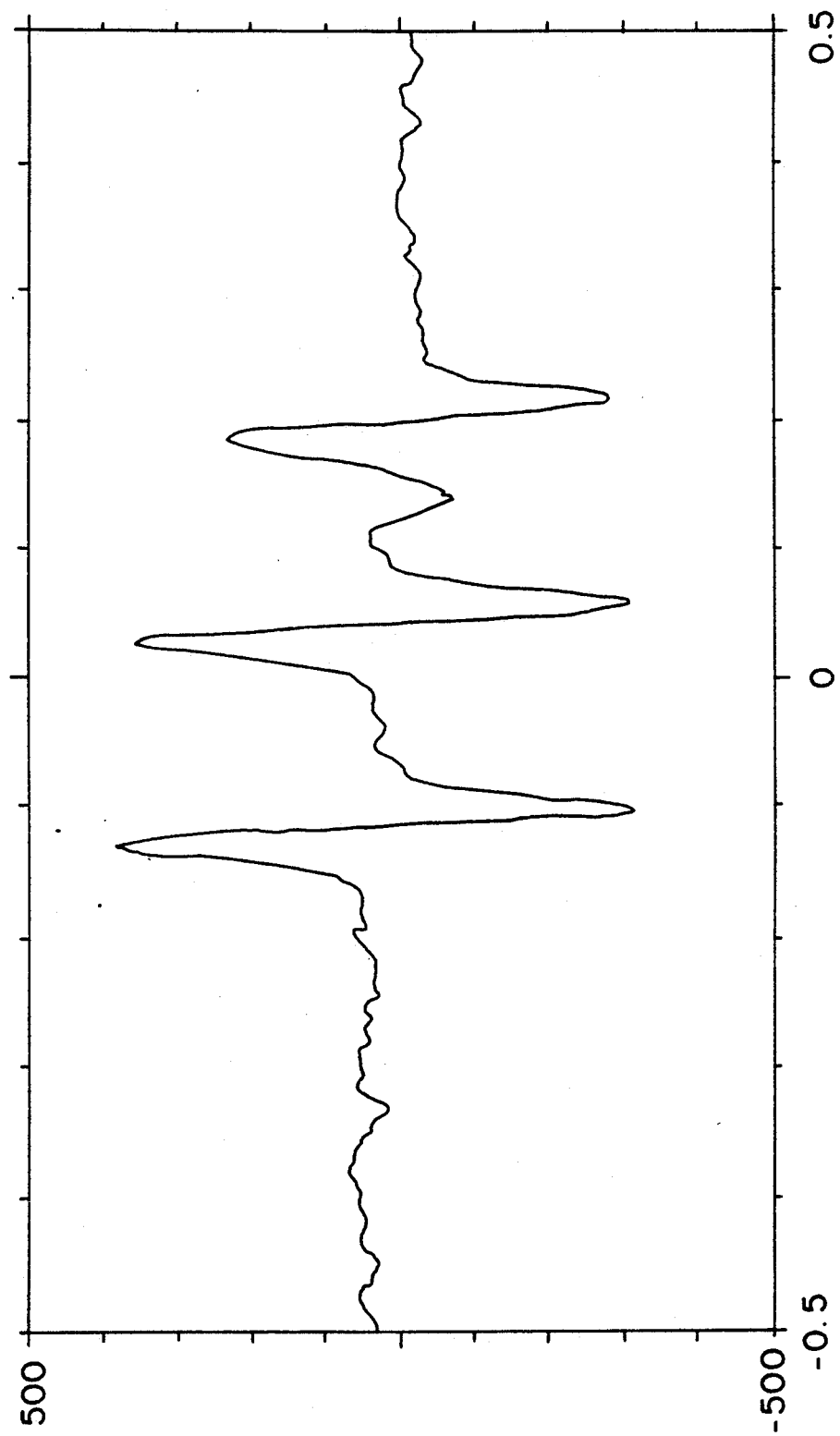
FIG. 6 shows ESR spectrum of TEMPO-ADAC, 8, at $10^{-6}$M in dimethylsulfoxide (Varian E-line spectrophotometer).
Figure 7A:
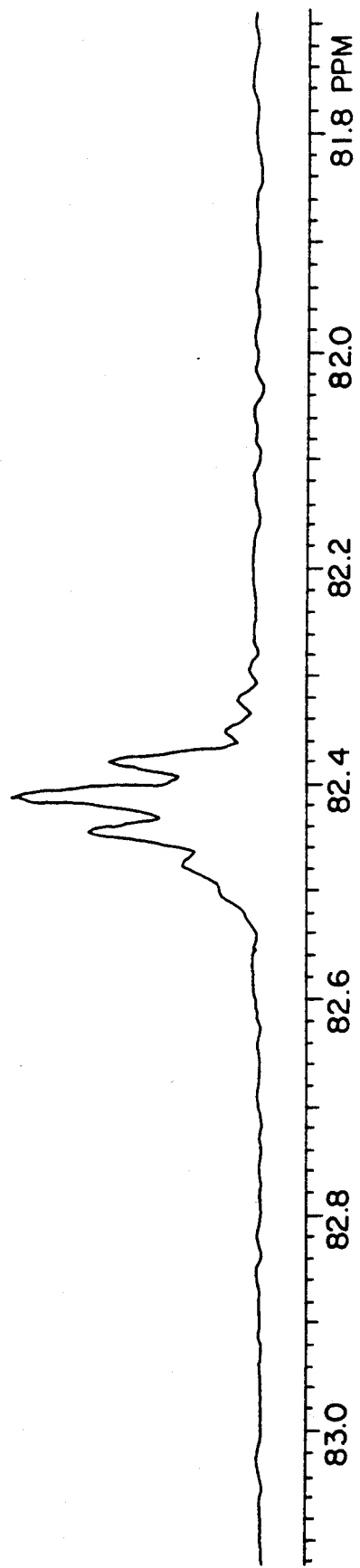
FIG. 7 (a) shows $^{19}$F NMR spectra of compound 10.
Figure 7B:
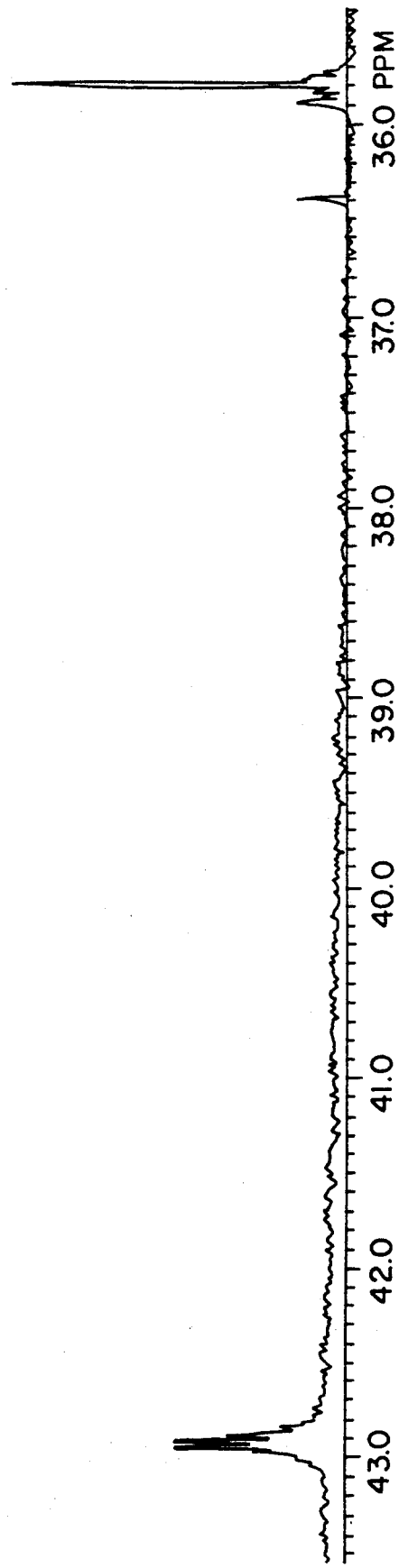
Figure 8:
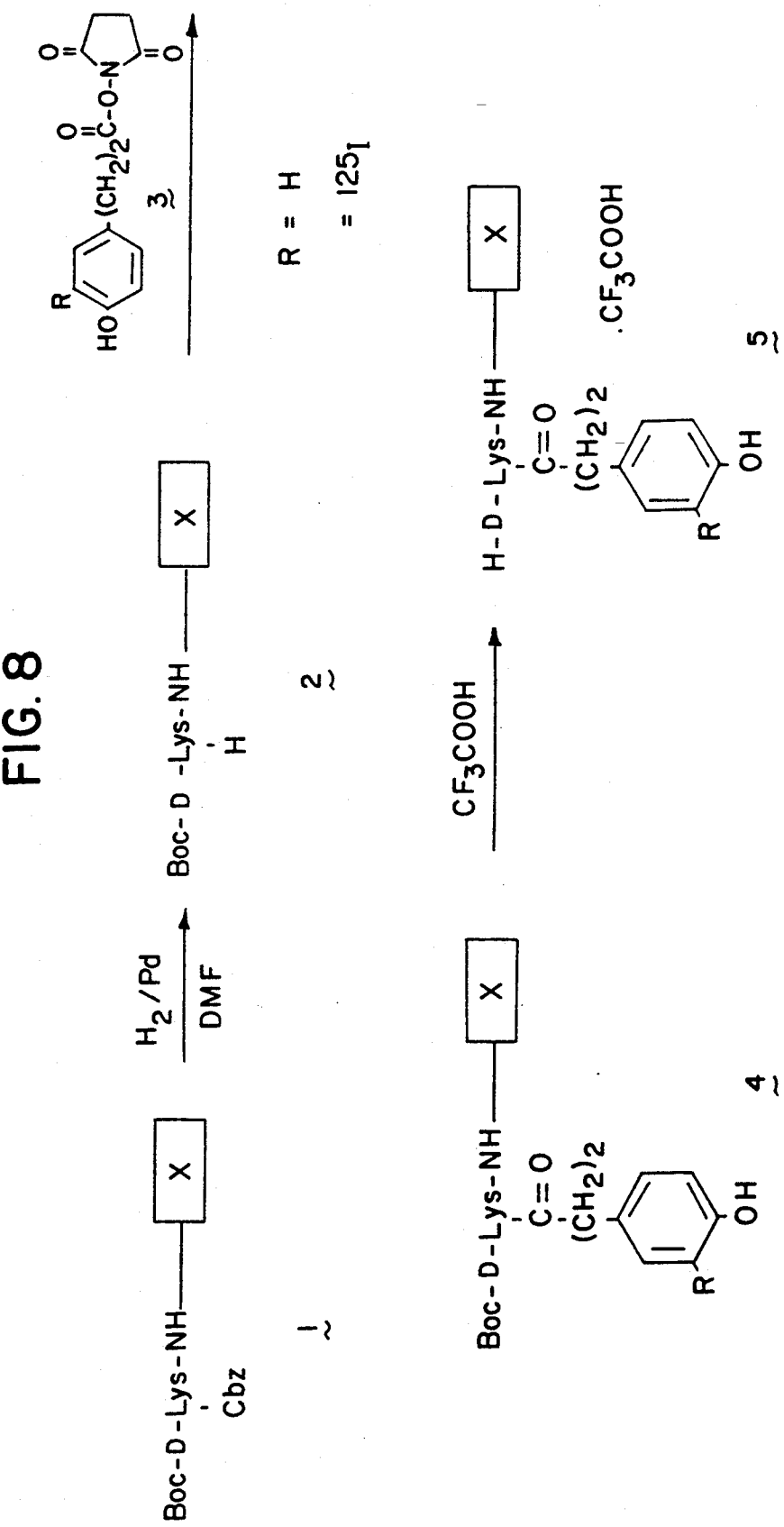
FIG. 8 shows the radioiodination of an amino acid conjugate using a prosthetic group.

Radioactive and non-radioactive assay-type probes are provided for enhancing the sensitivity of quantitative determination of adenosine amine congeners, which are agonists for A-1 and A-2 adenosine receptors and the sensitivity for quantitative analysis of xanthine amine congeners, which are antagonists for A-1 and A-2 receptors, these probes are prepared by reacting a fluorescent dye marker, or electron spin marker, or a $^{19}$F-NMR probe, or a radioactive $^{18}$F isotope marker or a radioactive iodine marker, or a metal complexing agent to introduce heavy metals such as technetium (99 m) or indium (113 m or 111). The congeners provide distal labeling sites and the receptor binding properties of the adenosine and xanthine compounds are retained. The congener approach permits higher potency for receptor binding in both agonist and antagonist types yet works great improvements in detection, assay, and characterization of receptors, and in biological binding studies for radioactive and spectroscopic detection.

Generalized Procedure. The general utility of labeling with radioactive and non-radioactive markers is illustrated for a typical agonist model, and $N^6$-phenyladenosine shown in Example 5 of abandoned application Ser. No. 717,624 and in the reaction scheme (Scheme 1) appearing herein as compound 8, namely, adenosine-$N^6$-(4'-carboxymethyl)phenyl-p-aminophenyl acetyl diaminoethane. This labeling utility is also shown for a typical antagonist model, a 1,3 dialkyl-xanthine-8-p-substitute phenyl congener exemplified in applications, Ser. No. 664,953 filed May 26, 1984, now U.S. Pat. No. 4,612,315 and Ser. No. 717,616 filed Mar. 29, 1985, now U.S. Pat. No. 4,696,932 this model antagonist being 8-(4'-carboxymethyloxyphenyl)-1,3 dipropyl xanthine aminoethylamide and being disclosed in U.S. Pat. No. 4,612,315. The synthesis of the aforesaid $N^6$-phenyl adenosine compound is shown in abandoned application Ser. No. 717,624, and the synthesis of the aforesaid xanthine congener compound is shown in U.S. Pat. No. 4,612,315.

The scope of xanthine congeners used as intermediates to make probes is shown below.

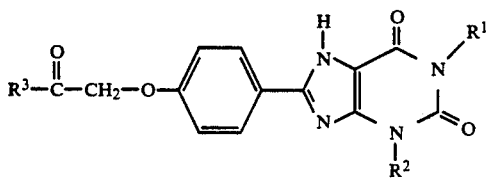

wherein $R^1$ and $R^2$ = an alkyl of 1–6 carbon atoms;
$R^3$ = hydroxy, alkoxy of 1 to 4 carbon atoms, phenoxy, N-succinimide; or
wherein $R^3 = R^4R^5N$
  wherein $R^5$ is hydrogen, alkyl of 1 to 4 carbon atoms, phenyl or alkylaryl groups wherein the alkyl contains 1 to 4 carbon atoms and the aryl is phenyl; and
  wherein $R^4 = R^5$ or $x(CH_2)n$—
    wherein x = primary, secondary, or tertiary amino group wherein the substituents are hydrogen, alkyl containing 1–6 carbon atoms or alkylaryl wherein the alkyl contains 1–6 carbon atoms and the aryl is phenyl; or secondary or tertiary amino group wherein one of the amine substituents is a p-hydroxybenzyl group or hydroxy or carboxy or acyl-amino group of the form $R^6NH$ and the other is lower akyl;
      wherein $R^6$ = a carboxyalkyl group having 1–6 carbon atoms optionally substituted with at least one halogen; or naturally occurring alpha-amino acids of the L configuration or their D configuration isomers or
  N-benzyloxycarbonyl alpha-amino acid of the L or D configuration; or biotin, bonded through the amide linkage directly or through an amide linkage to a naturally occurring alpha-amino acid having between 2 and 6 carbon atoms or
  2-thiopheneacetic acid through the carboxyl group thereof;
  n = 1-10
and pharmaceutically acceptable salts.

Other xanthine congeners have the general formula:

A—B where A and B are linked together in an amide linkage, and where A (the primary pharmacophore) is:

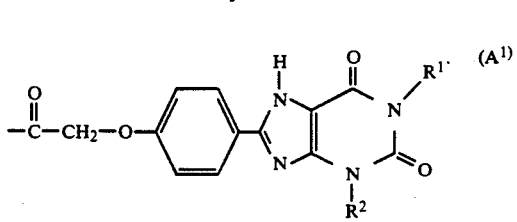

or

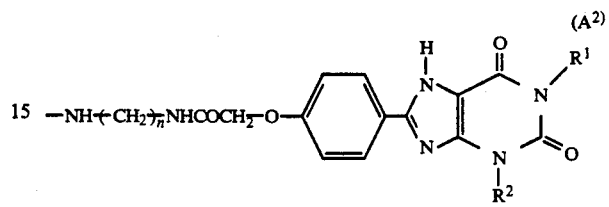

where $R^1$ and $R^2$ are alkyl of 1–6 carbons and n = 2–6; and
where B (the carrier) is a natural amino acid of the L-series or D- configuration or an oligopeptide consisting of 1–5 natural amino acids of the L- series or D- configuration, or an oligopeptide derivative of 3(2'-thienyl)alanine, these last named oligopeptides being linked through the amide linkage.

Scope of adenosine congener compounds used as intermediates to make probes. The congener compounds are in the scope stated in copending application Ser. No. 833,035 filed Feb. 23, 1986, as indicated below:

The compounds of the present invention which are used for treating animals and achieving coronary vasodilation are selected from the following formula.

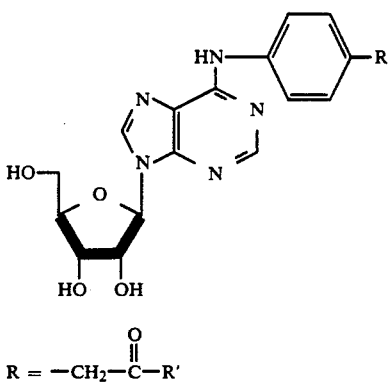

$$R = -CH_2-\overset{O}{\underset{\|}{C}}-R'$$

wherein R' is hydroxyl, lower alkylamino, monoarylamine (alkyl or aryl groups are optionally substituted with methyl, halolower alkyl, lower alkyl, ester, or amino groups), or an oligopeptide (up to five amino acids in length, optionally protected on the alpha-amino and alpha-carboxylate functionality by conventional peptide blocking groups) in which the point of attachment is through an amide bond at the p-position of phenylalanine;

$$R = -CH_2\overset{O}{\underset{\|}{C}}NH-\underset{}{\bigcirc}-CH_2-\overset{O}{\underset{\|}{C}}-R''$$

wherein R'' is alkoxy, lower alkylamino (optionally substituted with amino or acylamino groups) or

R''=NH—(CH$_2$)$_2$NHR''' wherein R'''= is an acyl group including acetyl or p-hydroxyphenylpropionyl or d-biotinyl or alpha-bromoacetyl, methyl fumaryl, d-biotinyl-ε-aminocaproyl, or an amino acid of the L- or D-configuration, or R''' is a monoaryl group, or R'' is NH(CH$_2$)$_2$N=C=S.

Scheme I

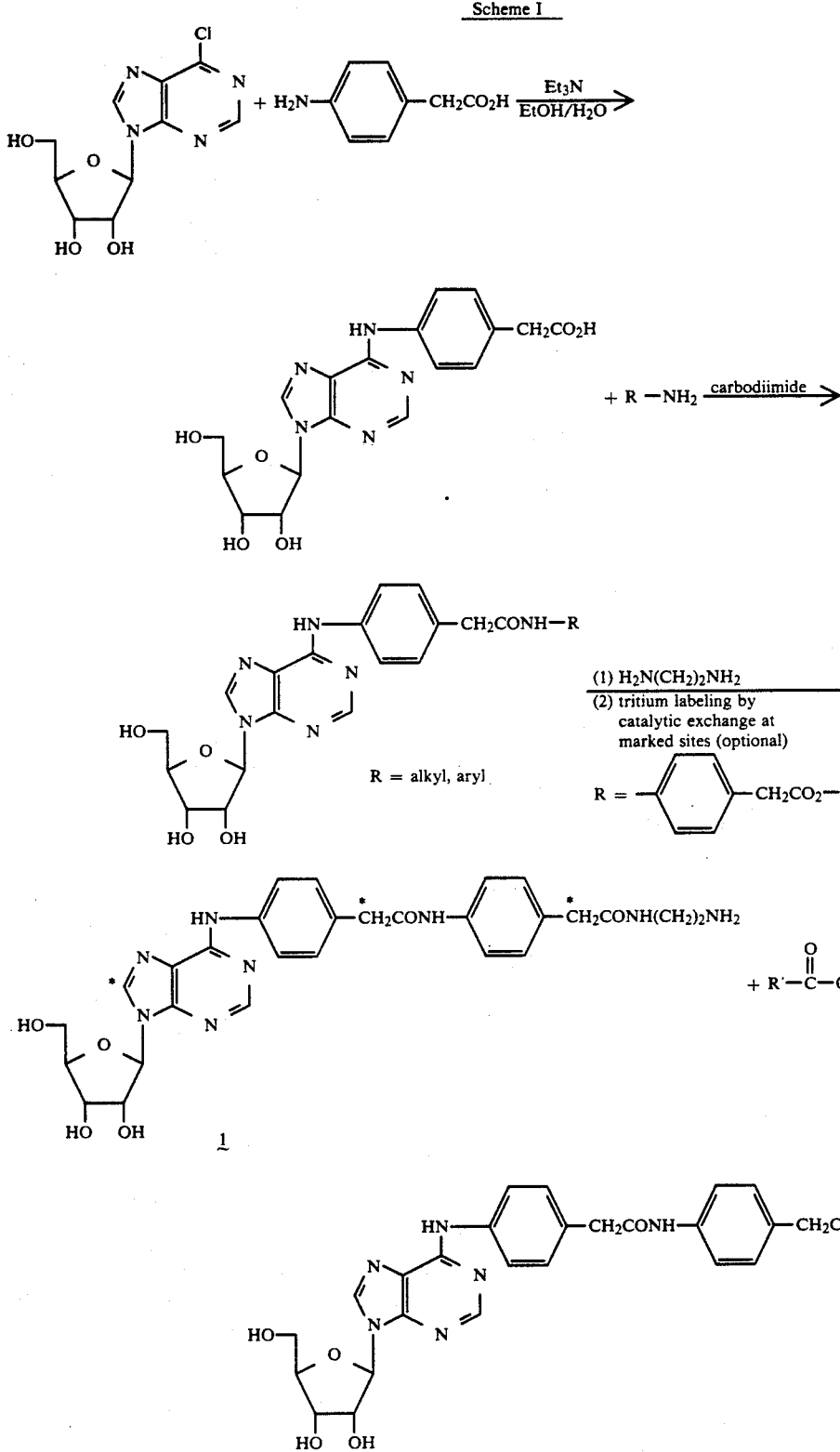

The specific model agonist is identified by the acronym ADAC and the specific model antagonist by the acronym XAC. In the above Scheme 1, compound 8 has 3 carbon atoms marked with an asterisk and these carbon atoms are tritium labeling sites.

Fluorescent Probes

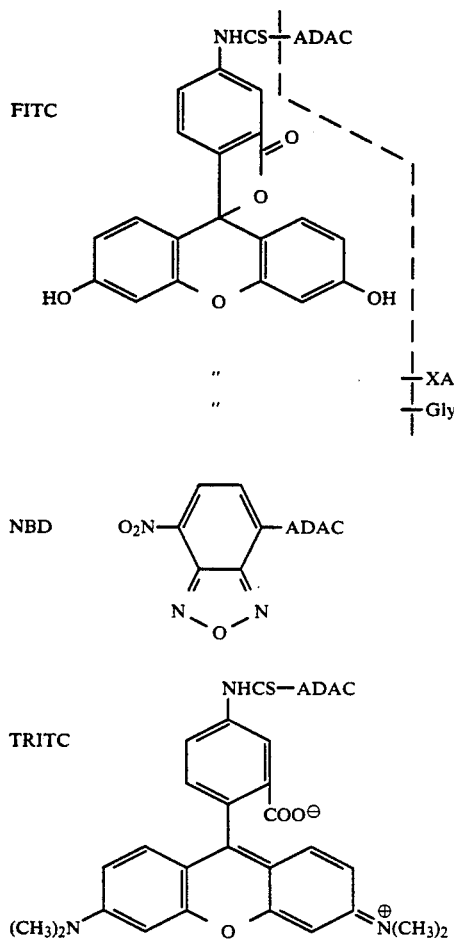

FITC   NHCS—ADAC   3
"      XAC   4
"      Gly₃—XAC   5

NBD

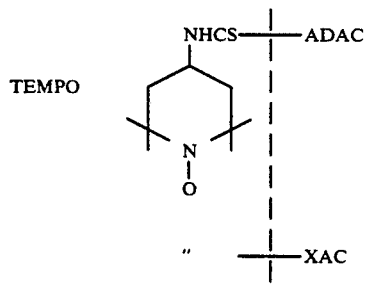

O₂N—[ring]—ADAC   6

TRITC   NHCS—ADAC   7

Spin Label Probes

TEMPO   NHCS—ADAC   8
"       XAC        9

¹⁹F—NMR Probes

TFA    CF₃CO—XAC         10
HFB    CF₃CF₂CF₂CO—XAC   11

Metal Complexing Probes

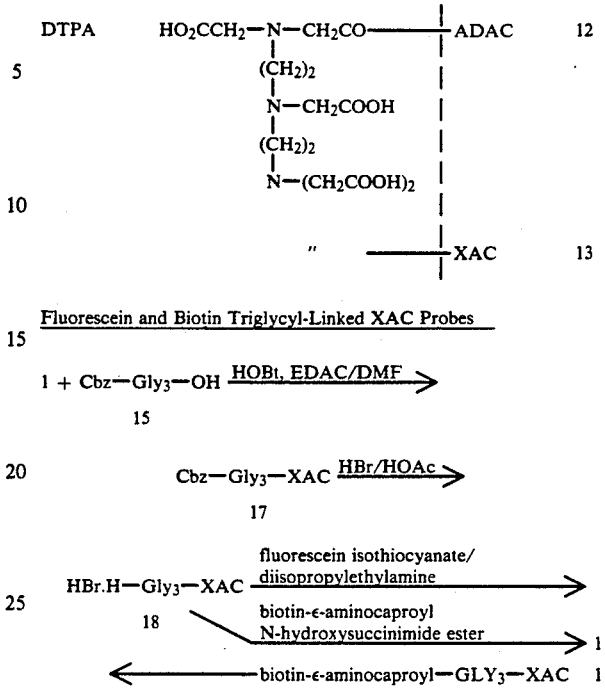

DTPA   HO₂CCH₂—N—CH₂CO—ADAC   12
              |
              (CH₂)₂
              |
              N—CH₂COOH
              |
              (CH₂)₂
              |
              N—(CH₂COOH)₂

"   ——XAC   13

Fluorescein and Biotin Triglycyl-Linked XAC Probes

1 + Cbz—Gly₃—OH  $\xrightarrow{\text{HOBt, EDAC/DMF}}$
                          15

Cbz—Gly₃—XAC  $\xrightarrow{\text{HBr/HOAc}}$
     17

HBr.H—Gly₃—XAC  $\xrightarrow{\text{fluorescein isothiocyanate/diisopropylethylamine}}$
     18         $\xrightarrow{\text{biotin-ε-aminocaproyl N-hydroxysuccinimide ester}}$ 1

$\xleftarrow{\phantom{xxxxxxx}}$ biotin-ε-aminocaproyl—GLY₃—XAC   1

In the diagram above, there are illustrated fluorescent probes, fluorescein isothiocyanate coupled to ADAC model compound above as assay-type compound 3, fluorescein isothiocyanate coupled to XAC model compound as assay-type compound 4, and fluorescein isothiocyanate coupled to triglycidyl linked XAC model compound as assay-type compound 5.

Nitrobenzoxadiazole linked to model compound ADAC is shown as compound 6, wherein the NBD fluorescent marker is shown at the left side and ADAC on the right side of the diagram, in the same manner as FITC (fluorescein isothiocyanate) is shown at the left for compounds 3, 4 and 5.

Fluorescent analogs of adenosine receptors have a variety of applications. For example, spectral changes of fluorescent analogs may be used to characterize receptor properties in combination assisted with different functional states, accessibility of sites by fluorescent quenching and an energizing transfer of receptors in membranes using fluorescent photobleaching of NBD derivatives such as compound 6.

Tetramethylrhodamine conjugate with ADAC model compound is shown in the diagram as compound 7. Compounds 3–7 are representative of the fluorescent label examples which have been made.

Spin label probes are shown in the diagram for ADAC using TEMPO (2,2,6,6 tetramethylpiperidinyloxy 4-isothiocyanate) (Aldrich Chemical Co.) to make compound 8 and with XAC to make compound 9.

Nuclear magnetic resonance using the ¹⁹F isotope of fluorine are shown as compounds 10 and 11, both of these being especially suitable for nuclear magnetic resonance studies. The labeling reagent TFA is ethyl trifluoroacetate having the ¹⁹F isotope present (commercially available) and the reagent HFA is heptafluorobutrnylanhydride having the ¹⁹F isotope, also commercially available. The NMR probes produced compounds 10 and 11 are both examples of labeled XAC compounds but could easily be extended to labeled to ADAC compounds.

A metal complexing probe based upon diethylenetriamine pentacetic anhydride, shown in the diagram as DTPA coupling to ADAC is shown herein as compound 12 and when coupled to XAC is shown herein as compound 13.

Table 1 below summarizes the labeling procedures shown in the diagram and Table 2 below shows the potency of the labeled probes identified in the diagram and in Table 1 at A-1 adenosine receptors in 2 species, e.g., rat brain and bovine brain.

Halogen containing probes are of special significance in this invention. Notably $^{18}F$, $^{19}F$, and $^{125}I$ tagging has been found to have import. The $^{18}F$ subject matter is described in our application Ser. No. 717,616 filed Mar. 29, 1985, now U.S. Pat. No. 4,696,932 at page 4 as a positron emitter utilizing PETT. Of similar significance is $^{19}F$ which is described previous to the filing of the present application where the radioactive probe using the $^{19}F$ isotope of fluorine is deemed especially suitable for NMR nuclear magnetic resonance studies. Also of value are probes utilizing $^{125}I$ as radioactive labels and described in application Ser. No. 664,953 filed Oct. 26, 1984, now U.S. Pat. No. 4,612,315 at page 3.

Parabromethyl benzoyl groups may be linked to an $^{18}F$ group and thus undergo fluorination to become $^{18}F$ probes.

For development of PETT scanning agents in probing, the p-bromomethyl benzoyl group may be linked to amino groups present on pre-synthesized functionalized congeners, via its N-hydroxysuccinimide ester. The bromide is displaced readily by fluoride ion in acetonitrile under conditions similar to those used in 18F radiotracer studies. An example of the above is p-bromomethyl benzoyl group as a prosthetic group for the rapid introduction of fluorine. N-Succinimidyl-p-(bromomethyl)benzoate was prepared by condensing N-hydroxysuccinimide and p-(bromomethyl)benzoic acid in DMF/ethyl acetate (1:1) using one equivalent of dicyclohexyl-carbodiimide. After filtration of the urea, the product (70%) precipitated on addition of petroleum ether. Combination of this reagent with simple amines or with amine congeners of xanthines and adenosines in DMF led to efficient coupling to give labeled compounds as desired.

TABLE 1

[$^3$H]ADAC Binding to Cerebral Cortex Membrane

| | Ki(nM) | |
|---|---|---|
| | Rat | Calf |
| CHA | 1.2 (0.65–2.4) | 1.15 (0.45–2.3) |
| ADAC | 1.3 (0.92–1.93) | 0.46 (0.19–1.1) |
| R—PIA | 1.3 (0.84–2.1) | 0.78 (0.30–2.0) |
| NECA | 8.6 (4.5–16.5) | 4.9 (2.2–11.2) |
| XAC | 1.4 (0.86–2.3) | 0.14 (0.07–0.27) |
| 1,3-Dipropyl-8-phenyl | 9.2 (4.3–193) | 0.17 (0.06–0.46) |
| 8-Phenyl-theophylline | 66 (45–96) | 6.8 (3.0–15.5) |
| 8-p-Sulfophenyl 1,3-dipropylxanthine | 100 (82–130) | 24.5 (20.6–29.1) |
| 8-p-sulfophenyl theophylline | 750 (670–830) | 250 (210–290) |
| Theophylline | 12,400 (7600–20,400) | 12,500 (5300–29,600) |
| Dipyridamole | 28,700 (26,100–31,500) | >100,000 (27.8%) |
| Adenine | >100,000 (42%) | >100,000 (6.4%) |
| 2'5'-Dideoxy-adenosine | >100,000 (40%) | >100,000 (8.8%) |
| ATP | >100,000 (35%) | >100,000 (10.9%) |
| Inosine | >100,000 (20.6%) | >100,000 (1.5%) |
| Caffeine | 41,000 (29,00–60,000) | 41,000 (28,000–86,000) |
| 8-Phenyl-caffeine | 14,000 (12,000–16,000) | 8,300 (5,600–12,000) |
| 1,3-Dipropylxanthine | 710 (660–770) | 370 (230–590) |
| $N^6$-Benzylado | 220 (180–270) | 58 (45–74) |
| S—PIA | 52 (45–60) | 11.3 (9.1–14.1) |
| 2-Phenethylado | 17.5 (16.5–18.5) | 2.9 (2.3–36) |
| Adenosine-$N^6$— 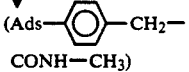 | 15.2 (11.0–21.0) | 2.9 (2.6–3.1) |
| 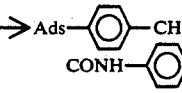 | 3.2 | 1.0 |
|  ADAC | 1.3 | 0.46 |
|  Ads | 20.2 | 3.2 |

Competition of [$^3$H]ADAC binding to rat and calf cerebral cortex membranes. Data are presented as geometric means, 95% confidence limits in parenthesis from 3–4 experiments. For values above, the percentage inhibition [$^3$H]ADAC binding is given in parenthesis.
R—PIA is R—$N^6$-phenylisopropyl adenosine.
CHA is $N^6$-cyclohexyladenosine whose properties and assay are described in Daly et al, Cell Mol. Neurobiol., vol. 3, p. 6 (1983).
NECA is 5'-N-ethylcarboxamide-adenosine.

TABLE 2
POTENCY OF BINDING OF MOLECULAR PROBES AT $A_1$-ADENOSINE RECEPTORS IN TWO SPECIES

| Compound | $K_i$(nM), rat brain | $K_i$(nM), bovine brain | $K_i$(rat)/$K_i$(bovine) |
|---|---|---|---|
| 3 | 7.1 ± 0.3 | 2.85 ± 0.15 | 2.5 |
| 4 | 125 ± 27 | 9.3 ± 0.10 | 13.4 |
| 5 | 96.5 ± 33.5 | 16.7 ± 0.20 | 5.8 |
| 6 | 4.3 ± 0.10 | 1.6 ± 0.0 | 2.7 |
| 7 | 41.6 ± 6.5 | 12.9 ± 2.1 | 3.2 |
| 8 | 4.4 ± 0.15 | 1.4 ± 0.2 | 3.1 |
| 9 | 4.9 ± 1.5 | 0.30 ± 0.12 | 16 |
| 10 | 4.6 ± 0.45 | 0.34 ± 0.04 | 14 |
| 11 | 8.1 ± 1.2 | 0.83 ± 0.06 | 9.8 |
| 12 | 109 ± 6.0 | 24.2 ± 115 | 4.5 |
| 13 | 59.5 ± 20.5 | 3.25 ± 0.75 | 18 |
| 15 | 49.5 ± 4.5 | 2.95 ± 0.35 | 16.9 |

Examples of the preferred embodiments are:

EXAMPLE 1

Unlabeled ADAC model compounds (see Scheme I, compound 9). Unlabeled ADAC intermediate was made by first reacting adenosine $N^6$-(4'-carboxymethyl)phenyl p-aminophenyl ester (40.7 mg) with ethylene diamine (0.6 ml) in DMF under nitrogen overnight, triturating the resulting oil with methanol to produce a solid which was washed with ether and dried in vacuo at 80° C. to give a yield of 41 mg (96%) $[\alpha]_D^{25}$ −39.7° (DMF, c=0.7) UV spectrum shows peaks at 303, 251 and 241 nm. This is unlabeled ADAC compound of FIG. 1 herein.

Unlabeled XAC model compound 8-(4'-carboxymethyloxyphenyl)-1,3 dipropyl xanthine 2-aminoethylamide was made by the method shown in allowed co-pending application Ser. No. 664,953 filed Oct. 26, 1984.

Other materials. $N^6$-R-Phenylisopropyladenosine (R-PIA) and 5'-N-ethylcarboxamidoadenosine (NECA) were purchased from Research Biochemicals, Inc., Wayland, Mass. [$^3$H]$N^6$-R-Phenylisopropyladenosine (49.9 $C_i$/mmol) was purchased from New England Nuclear, Boston, Mass. Theophylline, adenine and inosine were from Sigma Chemical Company, St. Louis, Mo. 2',5'-Dideoxyadenosine was from P-L Biochemicals, Milwaukee, Wis., and dipyridamole was from Thomae, Biberach, FRG.

Preparation of [$^3$H]ADAC (2). Unlabeled ADAC (2), 7 mg, was dissolved in 0.1M sodium phosphate, pH 10, and subjected to catalytic exchange (9) using 100 mg of 5% PdO/BaSO$_4$ under 10 $C_i$ of tritium gas (carried out by Amersham Corp., England, procedure code TR.7). The catalyst was removed by filtration, and labile protons were exchanged, leaving 33 m$C_i$ of radio-activity, 25% of which co-migrated with ADAC by thin layer chromatography (Merck silica gel 60, CHCl$_3$:MeOH:-HOAc, 10:10:1, silica, R$_f$=0.14). Most of the radioactive impurities were less polar than ADAC. [$^3$H]ADAC (retention time 9.7 min) was purified by HPLC using an Altex Ultrasphere ODS 5u column (0.46×25 cm) with a mobile phase of 50% methanol in 10 mM triethylammonium trifluoroacetate (1.0 ml/min). The recovery for the purification step was 15%. Thus, the overall yield of isolated [$^3$H]ADAC (purity 96%) was only 0.4%. The concentration was determined by UV spectroscopy using an ε-value of 32,400 for the absorption peak at 303 nm. The specific activity was calculated to be 27.5 $C_i$/mmol.

The crude product from the tritium exchange reaction was also purified efficiently by ion exchange chromatography.

After dilution of the DMF solution with an equal volume of water, the mixture was passed over a cation exchange column (2 ml) in the hydrogen form (Amberlite IRC-50), and washed with 5 ml water. Elution with 2N ammonium hydroxide (1.0 ml) gave pure ADAC (20% of radioactivity applied to column). With unlabeled ADAC, this procedure resulted in 95% recovery.

EXAMPLE 2

Synthesis of fluorescent receptor probes. Fluorescein-containing probes 3–5, were synthesized by acylation of a dimethylformamide suspension (10–20 mg/ml) of the appropriate amine derivative with a 30–50% molar excess of a pure isomer of fluorescein isothiocyanate. The reactions were monitored by thin layer chromatography. When the free amine congener was no longer detectable, the solvent was evaporated under a stream of argon, and the product was isolated and purified by two crystallizations from methanol/ether.

Probes containing other covalently bound fluorescent dyes, e.g., 6 and 7, were prepared similarly from 7-chloro-4-nitrobenz-2-oxa-1,3-diazole chloride or from tetramethylrhodamine isocyanate, isomer R, respectively.

EXAMPLE 3

Spin label probes, 8 and 9, were prepared similarly from the appropriate amine functionalized congener, 2 or b 1, respectively, and 4-isothiocyanato-TEMPO (2,2,6,6,-tetramethyl-1-piperidinyloxy, free radical, Aldrich).

EXAMPLE 4

N-(Perfluoroalkylacyl) $^{19}$F NMR-probes, 10 and 11, were prepared from XAC and the corresponding perfluoroacyl ethyl ester, and the products were recrystallized from ethyl acetate/hexanes. Metal complexing probes, 12 and 13, were prepared similarly using diethylenetriaminepentacetic (DTPA) anhydride (Sigma).

EXAMPLE 5

Synthetic intermediate benzyloxycarbonyl-triglycyl-XAC (compound 17). Cbz-glycyl-glycyl-glycine (90 mg, 0.28 mmol, Sigma), XAC, 1 (42 mg, 0.10 mmol), and 1-hydroxybenzotriazole (30 mg, 0.22 mmol) were combined in 2 ml dimethylformamide and treated with 1-ethyl-3-(3-dimethyl-aminopropyl)-carbodiimide hydrochloride (80 mg, 0.37 mmol, Sigma). After the mixture was stirred for 24 hours, addition of 4 ml of H$_2$O caused the product, compound 17, to precipitate (73 mg, 100%). mp 229°–233° C. The product was homogeneous by thin layer chromatography, and the NMR spectrum was consistent with the structure.

Compound 17 was deprotected with 30% HBr/acetic acid for 1 hour at room temperature to give triglycyl-XAC hydrobromide, 18, in nearly quantitative yield. Mp. 250°–255° C.

EXAMPLE 6

Preparation of TEMPO-ADAC. ADAC, 2 (11.8 mg, 20 umol), was suspended in 0.5 ml DMF and treated with 4-isothiocyanato-TEMPO (2,2,6,6,-tetramethyl-1-piperidinyloxy, free radical (7 mg, Aldrich). After 1 hour 1.5 ml water was added to the solution, and the precipitate was collected, washed with a minimum of MeOH and ether, and recrystallized from DMF/ether/petroleum ether, to give a product which was homogeneous by thin layer chromatography and gave proton NMR and ESR spectra consistent with the structure. Yield 8.3 mg (51%). Cf-MS peak at 758 (m+1−MeO) and 626 (m+1 −ribose). IR shows a peak at 1580 cm$^{-1}$, characteristic of a thiourea carbonyl stretch.

EXAMPLE 7

Preparation of $^{19}$F compounds.

(a) N-Trifluoroacetyl-XAC (10). XAC, 1 (64 umol) was dissolved in a mixture of DMF (10 ml) and diisopropylethylamine (1 ml) and treated with $^{19}$F 1 ml ethyl trifluoroacetate. The reaction was warmed (50°) for 10 minutes. Upon addition of 10 ml H$_2$O, the product precipitated, giving 21 mg (64% yield) of N-trifluoroacetyl-XAC, mp 304°–306° C.

(b) N-Heptafluorobutyryl-XAC. Heptafluorobutyryl anhydride (0.5 ml, source) was added to a mixture of DMF (5 ml), EtOH (2 ml), and diisopropylethylamine (1 ml). XAC (50 mg) was added and the mixture was heated (50° C.) overnight. Water was added and the mixture was extracted three times with ethyl acetate. The organic layer was washed with sodium bicarbonate and pH 6 phosphate buffer and evaporated, leaving to solid product which was recrystallized from ethyl acetate petroleum ether in 68% yield.

Discussion of Examples 3, 6 and 7. ESR has been used widely to characterize binding to and conformational states of proteins and cell components. Nitroxide-bearing analogs of cholinergic agonists may be used to describe the kinetics of agonist-mediated transitions of membrane-bound nicotinic receptors. The agonist derivative TEMPO-ADAC, 8, and the antagonist derivative TEMPOXAC, 9, have high affinity at A$_1$ adenosine receptors. The 4-substituted TEMPO group was selected due to the absence of chiral centers, which would lead to diastereoisomers in adenosine conjugates. Given a sufficient quantity of receptor, compounds 8 and 9 are useful in electron spin resonance (ESR) studies.

Drug molecules containing fluorine have been used to probe interactions with macromolecules using $^{19}$F NMR. Fluorine can be introduced through a prosthetic labeling group coupled to a functionalized congener, e.g., the antagonist XAC, to give compounds 10 and 11. Due to the relatively low sensitivity of this instrumental method, to carry out $^{19}$F NMR with adenosine receptors would require purification of the receptor. However, in this regard, it should be noted that $^{19}$F NMR studies have already been reported for the 4-tri-fluoro-2,6-dinitrophenyl group fixed to whole cells.

EXAMPLE 8

Chelation. The strong chelator DTPA is used to complex a variety of heavy metal radioisotopes, such as indium and technetium, to proteins including monoclonal antibodies for diagnositc and therapeutic purposes. The DTPA prosthetic group makes available these heavy metal isotopes to make assay more sensitive.

EXAMPLE 9

Binding shown in Tables 1 and 2.

(a) Radioligand binding. The binding of [$^3$H]ADAC to cerebral cortex membranes from rat and calf was measured in a total volume of 1 ml containing 50 mM Tris-HCl, pH 7.4, 0.2 units adenosine deaminase and approximately 50–100 ug of membrane protein. The radio-ligand was routinely present in a final concentration of 1 nM. Other substances were added as indicated. Incubation was carried out at 37° C. for 120 min. All assays were done in triplicate. Bound and free radioligand were separated by addition of 4 ml of ice-cold incubation buffer followed by rapid filtration through Schleicher & Schuell GF/B glass fiber filters that had been treated with 0.3% polyethylenimine for 60 min. as described by Bruns et al herein. The filters were washed twice with 5 ml of ice-cold incubation buffer. For filtration, a Brandel M-24R manifold (Brandel Instruments, Gaithersburg, Md.) was used. Nonspecific binding of [$^3$H]ADAC was determined in the presence of 10 uM N$^6$-R-phenylisopropyl-adenosine (R-PIA). At 1 nM [$^3$H]ADAC nonspecific binding amounted to about 10–15% with rat and about 5% with calf cerebral cortex membranes. The same amount of nonspecific binding was obtained with 5 mM theophylline. Nonspecific binding of 1 nM [$^3$H]ADAC to filters amounted to about 4% of the total counts filtered with treated filters and was nearly completely eliminated with polyethylenimine-treated filters.

Binding of 1 nM [$^3$H]PIA to rat and calf cerebral cortex membranes was carried out in essentially in the same way. Nonspecific binding was less than 10% of total binding. Radioligand binding data were analyzed. Slope factors were determined from Hill plots ("pseudo-Hill" coefficients).

(a) Adenylate cyclase assay. Adenylate cyclase was assayed essentially as described in the method of Daly et al, *Cell Mol. Neurobiol.*, 3:69, 1983. Briefly stated, the medium contains 0.1 mM [alpha-$^{32}$p]ATP (0.3 uC$_i$/tube), 1 uM GTP, 1 mM MgCl$_2$, 0.1 mM cyclic AMP, 1 ug/ml adenosine deaminase, 0.1 mM rolipram (ZK 62,711), 1 mM EGTA, 5 mM creatine phosphate as the Tris-salt, 0.4 ug/ml creatine kinase, 2 mg/ml bovine serum albumin and 50 mM Tris-HCl, pH 7.4, in a total volume of 100 ul. Incubations were initiated by the addition of 10–15 ug of membrane protein and were conducted for 10 min. at 37° C. Cyclic AMP was purified. Inhibition of binding in a range of concentrations of each adenosine analog was done in triplicate for at least 2 separate experiments and IC$_{50}$ values were estimated graphically.

The tritiated form of an adenosine amine congener, ADAC (FIG. 1) was synthesized by the catalytic exchange method of Evans, et al. The method calls for the stirring of a nucleotide or saccharide derivatives in an aqueous medium (basic pH) in the presence of a large mass excess of a hydrogenation catalyst, 5% palladium oxide supported on barium sulfate. The chemical yield of the reaction, estimated to be20% before purification by HPLC, was lower than expected for this tritiation method, perhaps a result of adsorption of the product to the catalyst. There was no indication that the product, [$^3$H]ADAC, is particularly labile in aqueous buffer systems of moderate pH. Incorporation of the tritium label occurs most likely at a total of five positions, at the C-8 of adenine and at the benzylic positions resulting in a specific activity of 27.5 C$_i$/mmol.

The specific activity demonstrates saturable binding of [$^3$H]ADAC to rat and calf cerebral cortex membranes. In both tissues nonspecific binding increased linearly with radioligand concentrations. Specific [$^3$H]ADAC binding was saturable with B$_{max}$-values of 0.57 and 0.64 pmol/mg protein in rat and calf cerebral cortex, respectively. Nearly identical B$_{max}$-values have been obtained using the agonist ligand [$^3$H]PIA and the antagonist ligand [³H]XAC (4). Scatchard analysis reveals binding of [³H]ADAC to single binding sites. [³H]ADAC binds to rat cerebral cortex membranes with a $K_D$ of 1.4 nM. The binding affinity in calf cerebral cortex with a $K_D$ of 0.34 nM is about 4-fold higher.

Competition experiments with adenosine agonists and antagonists show that [³H]ADAC binding occurs to $A_1$ receptors. All of the competition curves are monophasic indicating an interaction at a single binding site. Due to the presence of low affinity agonist binding sites, some probes of the antagonist type may be preferred in some cases. Also, dipropyl groups are tritium labeled for XAC through reduction of 1,3-dialkylprecursor.

Fluorescent analogs of receptor ligands have a variety of applications. For example, spectral changes of fluorescent analogs have been used to characterize receptor properties in conformations associated with different functional states, accessibility of sites by fluorescence quenching, fluorescence depolarization, and energy transfer, and the distribution and lateral mobility of receptors in membranes using fluorescence photobleaching of NBD derivatives. The direct visualization of receptors for thyrotropin-releasing hormone on a tumor cell line using fluorescent drug analogs can be done. However, histochemical studies using fluorescent ligands for adrenergic and opiate receptors may reveal that the distribution of fluorescence does not reflect the labeling of receptor, but instead the occurrence of lipofuscin, an endogenous fluorescent compound.

Thus, the present invention has identified a fluorescein and NBD conjugates of ADAC, 3 and 6, respectively, as high affinity fluorescent ligands for $A_1$-adenosine receptors. The tetramethylrhodamine conjugate, 7, is only moderately potent at rat brain $A_1$-receptors. In the antagonist series, a pair of fluorescent conjugates of XAC, 4 and 5, differing only in the length of the spacer chain, were compared. These analogs are good candidates for a variety of studies such as described above, including fluorescent cell sorting to select populations of cells with a high density of receptors, and examining accessibility using quenching by antibodies to fluorescent dyes.

The fluorescein, rhodamine and NBD conjugates of ADAC and of XAC, above mentioned, illustrate only a few of the fluorescent dyes of the fluorescent types, most of which have brilliant hues in shades of green, yellow and violet. These fluorescent dyes known as xanthine dyes are substituted in the tricyclic aromatic ring with amino groups, hydroxy groups and amino hydroxy groups. The rhodamines are violet, the pyromines red, and fluorescein green. Fluorescein derivatives may be used, such as uramines or eosin (brominated fluorescein) or iodinated fluorescein; Rose Bengal may be used. In view of the great enhancement, any fluorescent dye maker in the above shade or hue may be employed.

Given a sufficiently long spacer group, the conjugates bind simultaneously to adenosine receptors and the glycoprotein AVIDIN (M. W. 66,000). This is an additional means of introducing spectroscopic probes when those moieties are coupled to AVIDIN. The conjugates of BIOTIN-ADAC bind to A-1 adenosine receptors with $K_\pm$ values of 11.4±0.4 and 36 nM in the absence and presence of saturating AVIDIN, respectively. The conjugate of BIOTIN— —AMINO—CAPROYL—ADAC binds to A-2 adenosine receptors in the absence and presence of saturating AVIDIN. This is described in Ser. No. 833,035, filed Feb. 26, 1986.

An outstanding benefit arises from the surprisingly high water solubility imparted by the functionalized congener in both ADAC and XAC, which aids in spectroscopic detection of very minute quantities.

| | | Process Summary of Examples | | | |
|---|---|---|---|---|---|
| Compound | Abbreviation | Method | Recryst. Solvent | % Yield | Mp (°C.) |
| 3 | FITC-ADAC | a | DMF/Et₂O | 73 | |
| 4 | FITC-XAC | a | MeOH/Et₂O/pet.ether | 60 | |
| 5 | FITC-Gly₃-XAC | a | MeOH/Et₂O | 67 | 191–194 dec |
| 6 | NBD-ADAC | b | DMF/MeOH/H₂O | 20 | 178–181 |
| 7 | TRITC-ADAC | a | DMF/MeOH/Et₂O | 57 | |
| 8 | TEMPO-ADAC | a | DMF/H₂O | 51 | dec begin 178 |
| 9 | TEMPO-XAC | a | DMF/Et₂O | 40 | |
| 10 | CF₃CO-XAC | d | DMF/H₂O | 64 | 304–306 |
| 11 | C₃F₇CO-XAC | d | EtOAc/pet.ether | 68 | |
| 12 | DTPA-ADAC | c | DMF/Meoh/Et₂O | 86 | |
| 13 | DTPA-XAC | c | MeOH/Et₂O | 48 | 179–182 dec | a - isothiocyanate.
b - aryl chloride.
c - carboxylic anhydride.
d - ethyl ester
dec - decomposition

We claim:
1. A probe molecule consisting of:
(1) an adenosine nucleus of the formula:

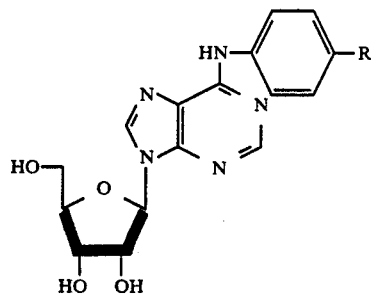

wherein R is —CH₂—C—R',
wherein R' is a member selected from the group consisting of hydroxyl, lower alkylamino, monoarylamine, and oligopeptide,
said alkyl and aryl groups of said lower alkylamino and said monoarylamine groups being unsubstituted or substituted with a member selected from the group consisting of methyl, halolower alkyl, lower alkyl carboxylate and amine groups and said oligopeptide being up to five amino acids in length in which the point of attachment of said oligopeptide is through an amide bond at the p-position of phenylalanine;
or wherein

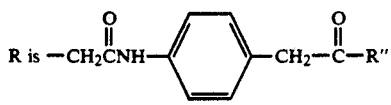

wherein R" is a member selected from the group consisting of NH)CH$_2$)$_2$N=C=S, alkoxy unsubstituted lower alkylamino, substituted lower alkylamino, and NH—(CH$_2$)$_2$NHR''', wherein said substituted lower alkylamino is substituted with an amino or lower alkyl acylamino group and R''' is a member selected from the group consisting of acetyl, p-hydroxyphenylpropionyl, d-biotinyl, alpha-bromo-acetyl, methyl fumaryl, d-biotinyl-ε-aminocaproyl, an amino acid of the L-configuration, an amino acid of the D-configuration and a monoaryl group; and (2) a label moiety bonded to said adenosine nucleus.

2. A probe as recited in claim 1, wherein said label is tritium.

3. A probe as recited in claim 1, wherein said label is a fluorescent dye.

4. A probe as recited in claim 3, wherein said fluorescent dye is tetramethylrhodamine.

5. A probe as recited in claim 3, wherein said fluorescent dye is fluorescein.

6. A probe as recited in claim 1, wherein said label is nitrobenzoxadiazole.

7. A probe as recited in claim 1, wherein said label is 2,2,6,6 tetramethyl-piperindinyloxy-4-isothiocyanate.

8. A probe as recited in claim 1, wherein said label comprises a complex of a metal atom or a metal ion and a chelating agent.

9. A probe as recited in claim 8, wherein said chelating agent is diethylenetriamine pentacetic anhydride.

10. A probe as recited in claim 8, wherein said metal ion is a radioactive isotope of technetium or indium.

11. A probe as recited in claim 1, wherein said label comprises a radioactive isotope selected from the group consisting of $^{18}$F, $^{19}$F and $^{125}$I.

12. The probe as recited in claim 11, wherein said label comprises $^{19}$F bonded to said adenosine nucleus by reacting the adenosine nucleus with ethyl trifluoroacetate or heptafluorobutyryl anhydride, wherein at least one of the fluorine atoms in a fluoro substituent is $^{19}$F.

13. A probe as recited in claim 11, wherein said label comprises $^{18}$F bonded to said adenosine nucleus by reacting said adenosine nucleus with a p-bromomethyl benzoyl intermediate.

14. A probe as recited in claim 1, wherein said label is bonded to said adenosine nucleus through a glycine linkage to an amine in the R group.

* * * * *